US008460531B2

(12) United States Patent
Amirkhanian et al.

(10) Patent No.: US 8,460,531 B2
(45) Date of Patent: *Jun. 11, 2013

(54) INTEGRATED BIO-ANALYSIS AND SAMPLE PREPARATION SYSTEM

(75) Inventors: Varouj Amirkhanian, La Crescenta, CA (US); Ming-Sun Liu, Brea, CA (US)

(73) Assignee: Qiagen Sciences, LLC, Germantown, MD (US)

( * ) Notice: Subject to any disclaimer, the term of this patent is extended or adjusted under 35 U.S.C. 154(b) by 133 days.

This patent is subject to a terminal disclaimer.

(21) Appl. No.: 12/961,362

(22) Filed: Dec. 6, 2010

(65) Prior Publication Data

US 2011/0155572 A1 Jun. 30, 2011

Related U.S. Application Data

(63) Continuation of application No. 10/973,828, filed on Oct. 25, 2004, now Pat. No. 7,846,315, and a continuation-in-part of application No. 10/059,993, filed on Jan. 28, 2002, now Pat. No. 7,309,409, and a continuation-in-part of application No. 10/060,052, filed on Jan. 28, 2002, now Pat. No. 6,828,567, and a continuation-in-part of application No. 10/319,803, filed on Dec. 13, 2002, now Pat. No. 7,250,099, and a continuation-in-part of application No. PCT/US03/39971, filed on Dec. 15, 2003, and a continuation-in-part of application No. 10/823,382, filed on Apr. 12, 2004, now Pat. No. 7,622,083.

(60) Provisional application No. 60/514,381, filed on Oct. 24, 2003.

(51) Int. Cl.
*G01N 27/00* (2006.01)
*G01N 33/48* (2006.01)

(52) U.S. Cl.
USPC .............................. 204/604; 205/792; 422/81

(58) Field of Classification Search
USPC ............. 204/604, 403.01, 600, 601; 205/775, 205/792; 422/62–67, 81, 602–607
See application file for complete search history.

(56) References Cited

U.S. PATENT DOCUMENTS 7,846,315 B2 * 12/2010 Amirkhanian et al. ....... 204/604

OTHER PUBLICATIONS

Belgrader et al. "Automated Sample Processing Using Robotics for Genetic Typing of Short Tandem Repeat Polymorphisms by Capillary Electrophoresis", Laboratory Robotics and Automation, vol. 9, No. 1, 1997, p. 3-7.*

* cited by examiner

*Primary Examiner* — J. Christopher Ball
(74) *Attorney, Agent, or Firm* — Liu & Liu

(57) ABSTRACT

An integrated bio-analysis system incorporates built-in sample preparation capabilities. In one aspect of the present invention, a bio-analysis instrument is provided with a built-in sample preparation device based on PCR (or thermal cycling block/module). In one embodiment of the present invention, a peltier unit in the sample preparation device provides thermal cycling of samples supported in a multi-well tray. In another aspect of the present invention, a CE instrument is provided with a built-in sample preparation capability, which may comprise a sample preparation (bio-molecular reaction) device based on thermal cycler type. In another aspect of the present invention, a PCR device is provided with a built-in analysis device, such as a CE device, for verifying the results of the PCR (bio-molecular reaction) process.

16 Claims, 5 Drawing Sheets

INTEGRATED BIO-ANALYSIS AND SAMPLE PREPARATION SYSTEM

This application is a Continuation of U.S. patent application Ser. No. 10/973,828, filed Oct. 25, 2004, which claims the priority of U.S. Provisional Patent Application No. 60/514,381, filed on Oct. 24, 2003. This Provisional patent application is fully incorporated by reference herein, as if fully set forth herein. The parent application is a Continuation-in-Part of U.S. patent application Ser. No. 10/059,993 entitled "Multi-Channel Bio-Separation Cartridge," filed on Jan. 28, 2002; and U.S. patent application Ser. No. 10/060,052, entitled "Optical Detection In A Multi-Channel Bio-Separation System", filed on Jan. 28, 2002; and U.S. patent application Ser. No. 10/319,803, entitled "Optical Detection Alignment Coupling Apparatus", filed on Dec. 13, 2002; and PCT Application No. PCT/US03/39971, entitled "Optical Detection Alignment Coupling Apparatus", filed on Dec. 15, 2003; and U.S. patent application Ser. No. 10/823,382, entitled "Multi-Capillary Electrophoresis Cartridge Interface Mechanism", filed on Apr. 12, 2004, which are all commonly assigned to BioCal Technology, Inc., the assignee of the present invention.

The above-mentioned applications, and all other applications, documents and references noted in the disclosure herein below, are fully incorporated by reference as if fully set forth herein.

BACKGROUND OF THE INVENTION

1. Field of the Invention

The present invention relates to bio-analysis, and more particularly a bio-analysis system integrating sample preparation process, and more particularly to a multi-channel bio-analysis system integrating sample preparation process.

2. Description of Related Art

Bioanalysis, such as DNA analysis, is rapidly making the transition from a purely scientific quest for accuracy to a routine procedure with increased and proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to ease sample handling during the process, and in general, to have a simplified, low cost, high sensitivity detector.

One type of DNA analysis instrument separates DNA molecules by relying on electrophoresis. Electrophoresis techniques could be used to separate fragments of DNA for genotyping applications, including human identity testing, expression analysis, pathogen detection, mutation detection, and pharmacogenetics studies. The term electrophoresis refers to the movement of a charged molecule under the influence of an electric field. Electrophoresis can be used to separate molecules that have equivalent charge-to-mass ratios but different masses. DNA fragments are one example of such molecules.

There are a variety of commercially available instruments applying electrophoresis to analyze DNA samples. One such type is a capillary electrophoresis (CE) instrument. By applying electrophoresis in a fused silica capillary column carrying a buffer solution, the sample size requirement is significantly smaller and the speed of separation and resolution can be increased multiple times compared to the slab gel-electrophoresis method. These DNA fragments in CE are often detected by directing light through the capillary wall, at the components separating from the sample that has been tagged with a fluorescence material, and detecting the fluorescence emissions induced by the incident light. The intensities of the emission are representative of the concentration, amount and/or size of the components of the sample. In the past, Laser-induced fluorescence (LIF) detection methods had been developed for CE instruments. Fluorescence detection is often the detection method of choice in the fields of genomics and proteomics because of its outstanding sensitivity compared to other detection methods.

Heretofore, CE instruments are designed to work with samples first prepared at other devices, and then loaded onto a sample tray in the CE instruments. Some of the sample preparation procedures could be quite involved, requiring manual and/or automatic procedures. Dedicated devices and systems have been designed to handle only sample preparation, involving steps such as sample extraction, purification, amplification, stabilization, etc., to produce samples that are suitable for separation by the CE instruments. For example, DNA samples may have to be prepared by a polymerase chain reaction (PCR) process, to amplify sufficient quantities of samples from a trace amount of DNA samples. The product of the PCR process may be subject to a CE process to verify the integrity or state of the result of the PCR process. The transfer from separately prepared samples to CE separation/analysis instruments require significant manual interventions, which affect overall throughput.

It would be desirable to develop a fully integrated bio-analysis system including built-in sample preparation process capabilities, to avoid user intervention during sample preparation and separation/analysis.

SUMMARY OF THE INVENTION

The present invention provides an integrated bio-analysis system with built-in sample preparation process capabilities. In one aspect of the present invention, a bio-analysis instrument is provided with a built-in sample preparation device. In one embodiment, the sample preparation process include a bio-molecular reaction process. In a particular embodiment, the bio-molecule reaction process is based on PCR. In a further embodiment of the present invention, a peltier unit in the sample preparation device provides thermal cycling of samples supported in a multi-well tray.

In another aspect of the present invention, a CE instrument is provided with a built-in sample preparation capability, which may comprise a bio-molecular reaction process, for example, a sample preparation device based on PCR.

In another aspect of the present invention, a bio-molecular reaction system is provided with a built-in analysis device, such as a CE device, for verifying the results of the reaction products, which may be modified bio-molecular samples. In a particular embodiment, the bio-molecule reaction system prepares samples based on PCR. In a further embodiment of the present invention, a thermal cycling unit is provided in the sample preparation device. The samples prepared by the PCR device may be used for other analysis in other systems.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF ILLUSTRATED EMBODIMENTS

Figure 1:
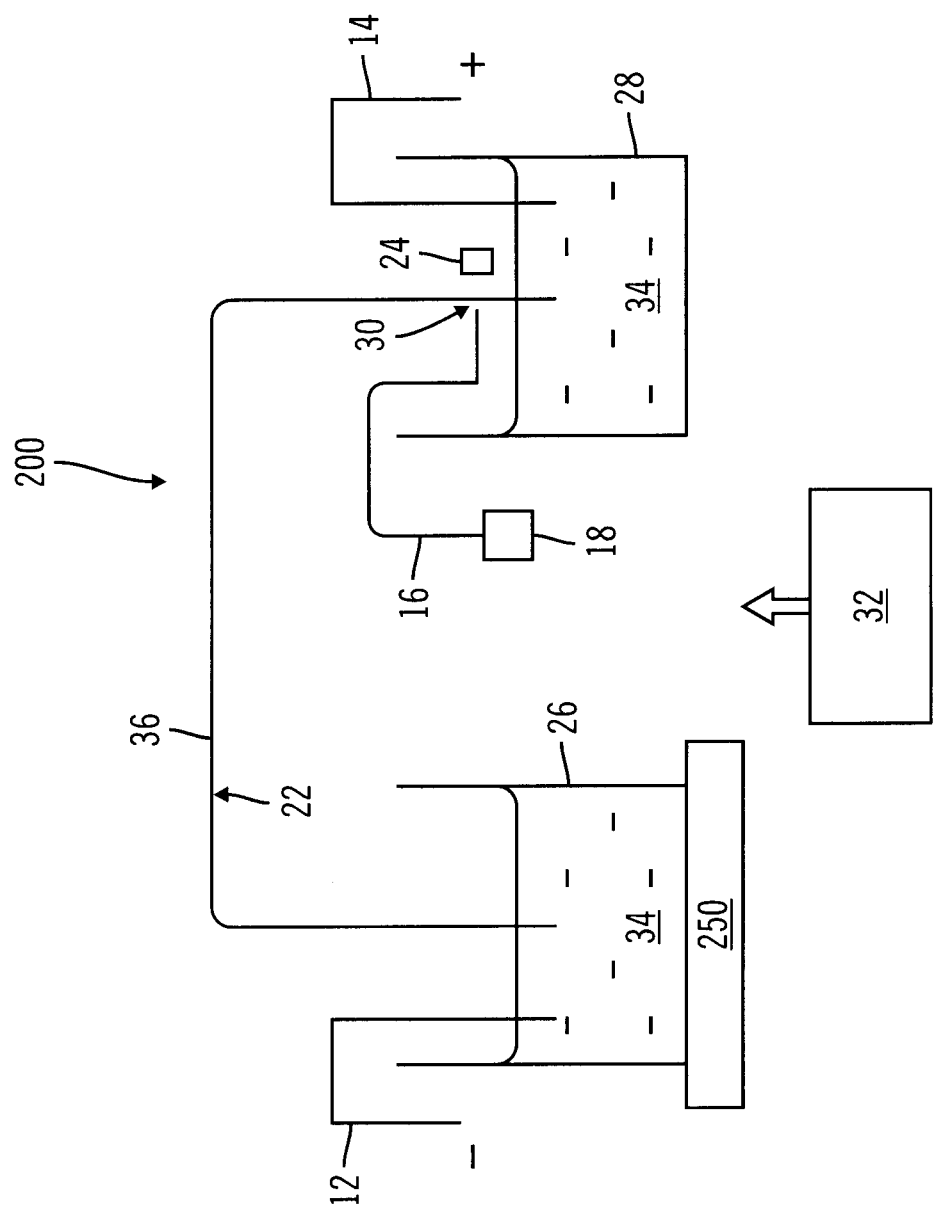
FIG. 1 is a schematic representation view of a capillary electrophoresis system that comprises a sample preparation device in accordance with one embodiment of the present invention.

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides for a bio-analysis system integrated with sample preparation. In one aspect of the present invention, a bio-analysis instrument is provided with a built-in sample preparation device. In one embodiment, the sample preparation process include a bio-molecular reaction process. In a particular embodiment, the bio-molecule reaction process is based on PCR. In another aspect of the present invention, a CE instrument is provided with a built-in sample preparation capability, which may comprise a bio-molecular reaction process, for example, a sample preparation device based on PCR. In another aspect of the present invention, a bio-molecular reaction system is provided with a built-in analysis device, such as a CE device, for verifying the results of the reaction products, which may be modified bio-molecular samples. In a particular embodiment, the bio-molecule reaction system prepares samples based on PCR. In a further embodiment of the present invention, a thermal cycling unit is provided in the sample preparation device. The samples prepared by the PCR device may be used for other analysis in other systems.

For purpose of illustrating the principles of the present invention and not by limitation, the present invention is described by reference to embodiments directed to CE analysis and PCR sample preparation. In the illustrated embodiment, the invention provides a fully integrated system of PCR sample preparation in an automated multi-channel CE system for genetic analysis.

Biocal Technology, Inc., the assignee of the present invention, developed a CE-based automated instrument (HDA-GT12 DNA Analyzer System). The illustrated embodiment of the inventive automated instrument is based on Biocal's CE instrument, which incorporates low-cost and sensitive optical detection technology, integrated reagents cartridge and micro-fluidic electrophoresis principle for a real-time fluorescent analysis, to form a sensitive and accurate bioagent detection (genetic analysis) system. The system is designed to be high-throughput, easy-to-use, portable, inexpensive, very robust and for field operation/applications.

The cartridge is designed to be supported by the instrument, with all essential cartridge elements aligned and coupled to support elements in the instrument. The cartridge is held with respect to sample trays that can be moved in relation to the capillary separation channels in the cartridge. The instrument is improved with the provision of a PCR based station to prepare samples from raw samples loaded into the system for separation and analysis, all within the same instrument, thereby minimizing further user intervention once raw samples (e.g., extracted DNA) have been loaded into the automated instrument, throughout the processes of sample preparation (DNA amplification/PCR), separation and analysis.

Figure 6:
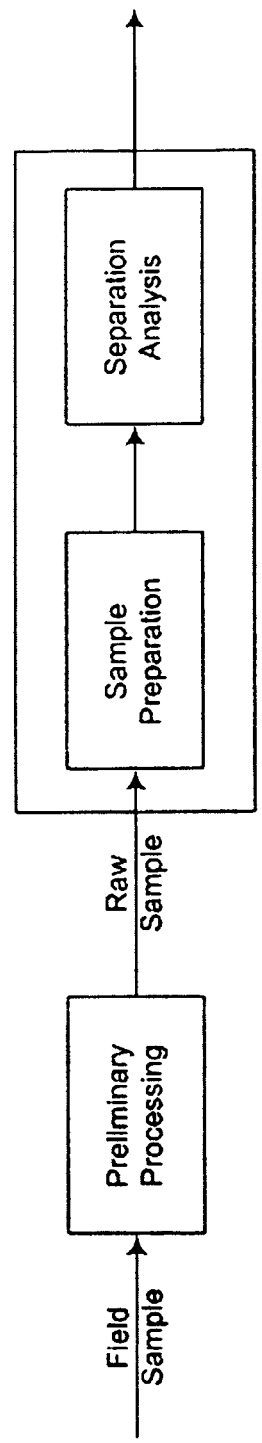
FIG. 6 is a schematic block diagram illustrating the relationship of various sample processing stages.

It is noted that in the context of the present invention, the raw sample (e.g., extracted DNA) may be an intermediate state or form of a sample taken in the field, which may have undergone prior preliminary preparation processes before being loaded into the sample preparation station in the automated system. In the context of the present invention, the raw sample undergoes a significant sample preparation process (e.g., PCR) in the automated instrument, which transforms the sample into a significantly different and/or modified form and/or state, beyond simply subjecting the raw sample to dilution, or other processes which merely presents the raw sample in a format that facilitates handling in subsequent processes. For example, the raw sample is subject to a biomolecular reaction process in the sample preparation device. FIG. 6 is a schematic block diagram illustrating the relationship of the various stages of processing discussed here. In reference to the subsequent separation and/or analysis processes, the resultant sample prepared by the sample preparation device is the input to the subsequent separation and/or analysis processes, and which is the sample subject to separation and/or analysis. The raw sample is the sample that is input to the sample preparation device, which is the sample subject to processing by the sample preparation device. The raw sample may be the product of prior preliminary processing.

For example, for a biological sample taken in the field, such as a saliva or blood of a subject, it is subject to preliminary processes, including without limitations extraction and purification, to obtain a DNA sample representative of the subject. Such extracted DNA fragment is the "raw sample", along with necessary chemicals (e.g., primers, polymerase, etc.), that is loaded into the integrated system 200 of the present invention (disclosed below), and more specifically the sample preparation device, such as for PCR amplification. The output of the PCR process is the sample for subsequent separation and/or analysis.

Overview of CE System

The system is designed and built for field robustness weighing no more than 40 lbs. The portable system also incorporates a built in modular and integrated PCR thermocycler with peltier cooler device for DNA amplification.

FIG. 1 is a schematic representation of a capillary electrophoresis (CE) system 200 in accordance with one embodiment of the present invention. The CE system 200 generally comprises a capillary separation column 22 (e.g., 200-500 µm O.D.), which defines a separation channel 36 (e.g., 25-200 µm I.D.). The capillary column 22 may be made of fused silica, glass, polyimide, or other plastic/ceramic/glassy materials. The inside walls of the separation column 22 (i.e., the walls of the separation channel 36) may be coated with a material that can build up an electrostatic charge to facilitate electrophoresis and/or electrokinetic migration of the sample components. The separation channel 36 is filled with a separation support medium, which may simply be a running buffer, or a sieving gel matrix known in the art. For radiation induced fluorescence detection, the gel matrix includes a known fluorophore, such as Ethidium Bromide.

One end of the capillary column 22 is submerged in a reservoir 28 of running buffer/gel 34. The other end of the capillary column 22 is coupled to the sample vial 26. It is understood that the detection configurations shown in the other embodiments can be equally implemented in a system similar to the CE system 200. Also, the separation channel 36 may be one straight capillary or micro-channel with a section of the detection window closest to the gel-reservoir at the exit end being the detection zone, which is the current preferred mode of our invention. A radiation detector 24 is positioned outside a transparent section of the capillary walls at detection zone 30. An excitation fiber 16 extends from a radiation source 18 (e.g., LED or laser) and is directed at the detection zone 30 outside the walls of the column. Electrodes 12 and 14, that are part of the cartridge assembly are coupled to the buffer reservoirs 26 and gel reservoir 28 to complete the electrophoresis path.

Figure 2:
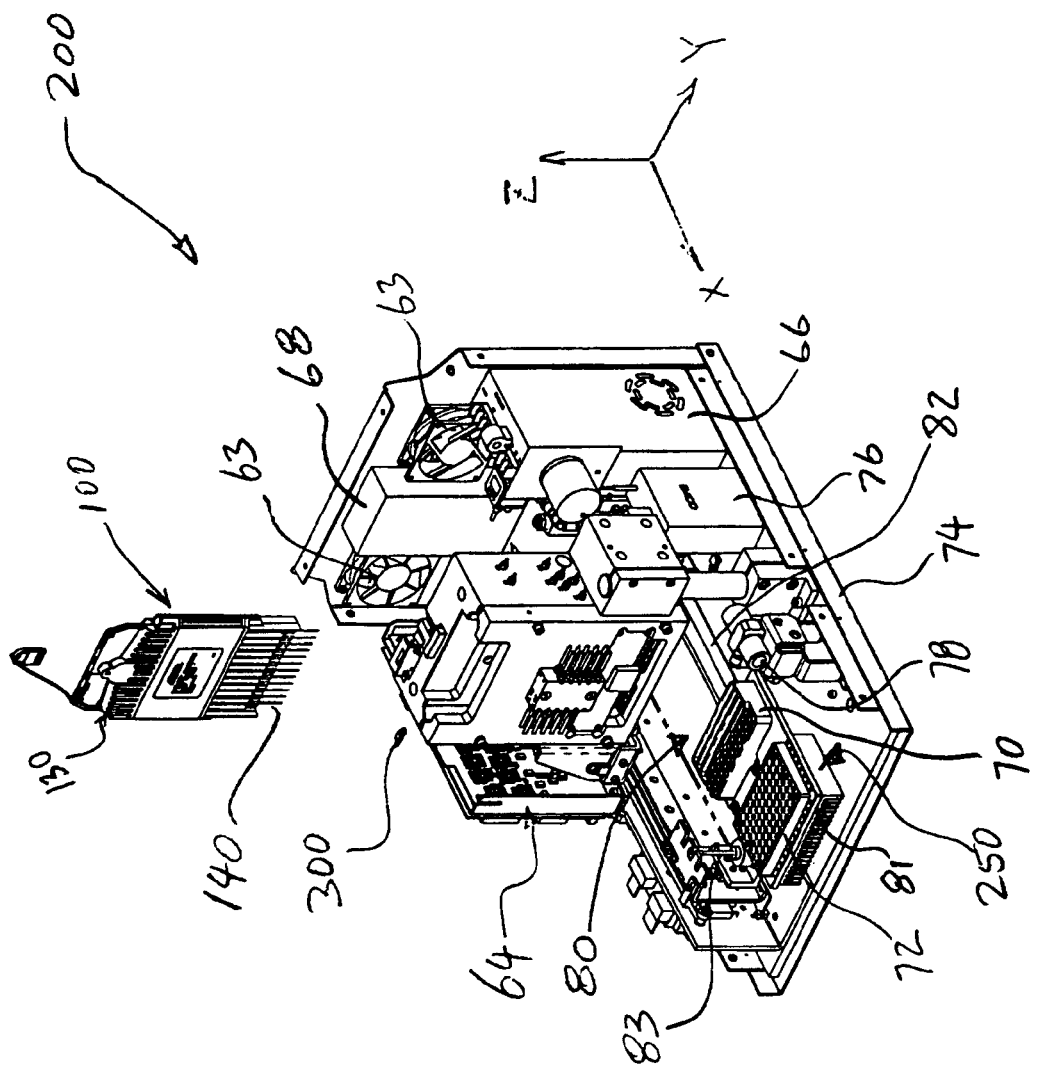
FIG. 2 is a perspective view of a capillary electrophoresis system that comprises a sample preparation device in accordance with one embodiment of the present invention.

In accordance with the present invention, the system 200 includes a sample preparation device 250. The illustrated embodiment in FIG. 2 shows a sample preparation device suitable for DNA amplification by PCR. In particular, the sample preparation device 250 comprises a thermal cycler for PCR (which comprises a heating/cooling element and a controller to effect the required heating and cooling conditions). The extracted biological molecules/DNA samples from the field (soil, air and water) are loaded onto the micro titer plate 72 along with the necessary chemistry and/or protocol, and amplified (e.g., in a bio-molecules reaction process of the sample preparation device) to allow easy detection during capillary electrophoresis. After the PCR process has been completed, the micro titer plate 72 is moved to under the capillary columns 140 and to move the cartridge 100 vertically to allow the capillary columns 140 to access the wells in the micro titer plate 72. The amplified DNA samples (PCR products) are then automatically manipulated and introduced by electro-kinetic injection through the micro-channels of the gel-cartridge for separation and fluorescence detection of molecules.

Overview of CE Separation and Analysis

In operation, a raw sample taken from the field is prepared (e.g., DNA is extracted, purified and then amplification by PCR) into a sample suitable for CE. For example, a prepared biological sample (e.g., a DNA sample) in the sample vial 26 prepared by the sample preparation device 250 (i.e., a DNA amplification device in the illustrated embodiment) is introduced into the far end of the capillary column 22 away from the detection zone 30 by any of a number of ways (e.g., electrokinetic injection from the sample reservoir). The sample binds to the fluorophore in the gel matrix supported in the capillary column 22.

When a DC potential (e.g., 1-30 KV) is applied between electrodes 12 and 14, the sample migrates under the applied electric potential along the separation channel 36 (e.g. DNA that is negatively charged travels through the sieving gel with an integrated dye matrix/fluorophore toward a positive electrode as shown in FIG. 1) and separates into bands of sample components (DNA fragments). The extent of separation and distance moved along the separation channel 36 depends on a number of factors, such as migration mobility of the sample components, the mass and size or length of the sample components, and the separation support medium. The driving forces in the separation channel 36 for the separation of samples could be electrophoretic, pressure, or electro-osmotic flow (EOF) means.

When the sample reaches the detection zone, excitation radiation is directed via the excitation fiber 16 at the detection zone. The sample components fluoresce with intensities proportional to the concentrations of the respective sample components (proportional to the amount of fluorescent tag material). The detector 24 detects the intensities of the emitted fluorescence at a wavelength different from that of the incident radiation. The detected emitted radiation may be analyzed by known methods. For an automated system, a controller 32 controls the operations of the CE system 200.

Overview of PCR

The purpose of a PCR is to make a large number of copies of a gene. This is necessary in order to have enough starting template for DNA fragment analysis by CE. Below is a brief explanation of the PCR thermal cycling reactions.

1. The Cycling Reaction:

There are three major steps in a PCR, which are repeated for 30 or 40 cycles. This is done on an automated cycler, which can heat and cool sample vials with the reaction mixture in a very short time. As will be described later below, a peltier cooler/heater type mechanism may be integrated as part of the transport carriage frame of the X-Y transport mechanism of the multi-channel capillary electrophoresis instrument for a complete solution of DNA amplification and analysis. DNA amplification by PCR is well known in the art. Details of the protocol and chemistry (e.g., primers, polymerase, etc.) are omitted from the discussion herein. Further references may be made to any of the well documented literatures in the field. In accordance with one embodiment of PCR, the three major steps in a PCR include:

1. Denaturation at 94° C.:

During the denaturation, the double strand melts open to single stranded DNA, all enzymatic reactions stop (for example: the extension from a previous cycle).

2. Annealing at 54° C.:

The primers are jiggling around, caused by the Brownian motion. Ionic bonds are constantly formed and broken between the single stranded primer and the single stranded template. The more stable bonds last a little bit longer (primers that fit exactly) and on that little piece of double stranded DNA (template and primer), the polymerase can attach and starts copying the template. Once there are a few bases built in, the ionic bond is so strong between the template and the primer, that it does not break anymore.

3. Extension at 72° C.:

This is the ideal working temperature for the polymerase. The primers, where there are a few bases built in, already have a stronger ionic attraction to the template than the forces breaking these attractions. Primers that are on positions with no exact match, get loose again (because of the higher temperature) and don't give an extension of the fragment.

The bases (complementary to the template) are coupled to the primer on the 3' side (the polymerase adds dNTP's from 5' to 3', reading the template from 3' to 5' side, bases are added complementary to the template). It is understood that the foregoing steps may be modified but nonetheless provides a PCR or DNA amplification, without departing from the scope and spirit of the present invention.

Multiple Capillary Cartridge Based CE System

In accordance with the present invention, for nucleic acid detection, PCR amplification is integrated into a micro-fluidic electrophoresis system. Raw samples of DNA or RNA extracted from the field are purified, then loaded (using standard PCR plate preparation steps) into sample vials (e.g., a 96-well micro titer plate) in the automatic micro-fluidic electrophoresis system for PCR amplification. Primer pairs for specific gene markers will be used for PCR analysis. Further in accordance with the present invention, the finished PCR products in the sample vials are automatically introduced to the multi-channel gel cartridge via electro-kinetic sample injection for high-resolution separation and fluorescence detection.

FIG. 2 shows an overall perspective view of the CE system 200 (e.g., an DNA Analyzer). The CE system 200 incorporates an interface mechanism 300, in accordance with one embodiment of the present invention. The interface mechanism 300 supports a multi-channel cartridge 100 in accordance with the one embodiment of the present invention, which provides easy handling of multi-channel separation columns, and allows easy optical coupling of the detection zones to the detection optics of the CE system 200. Details of the interface mechanism 300 may be referenced to U.S. patent application Ser. No. 10/823,382, which has been fully incorporated by reference herein. The fully automated DNA analysis system 200 has a base 74, supporting a modular X-Z mechanism 80 having a sample tray support frame 81. The X-Z mechanism 80 moves the PCR sample preparation device 250 (details disclosed later below in reference to FIGS. 4 and 5) that supports a 96-well micro-titer plate 72, and a buffer plate 70 in relation to the multi-capillary cartridge 100 supported by the interface mechanism 300. Specifically, the mechanism 80 comprises an X mechanism 82 for moving the support frame 81 along the X-direction relative to the cartridge 100, and a Z mechanism 83 for moving the cartridge in the Z direction relative to the support frame 81. The PCR sample preparation device 250 is controlled by a PCR thermoelectric controller 68.

PCR Sample Preparation Device

Figure 4:
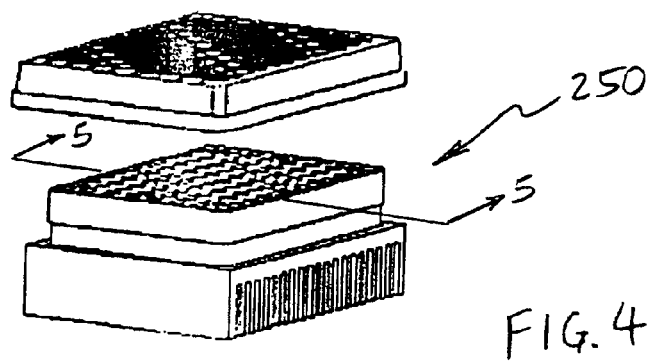
FIG. 4 is a perspective view of the sample preparation device.
Figure 5:
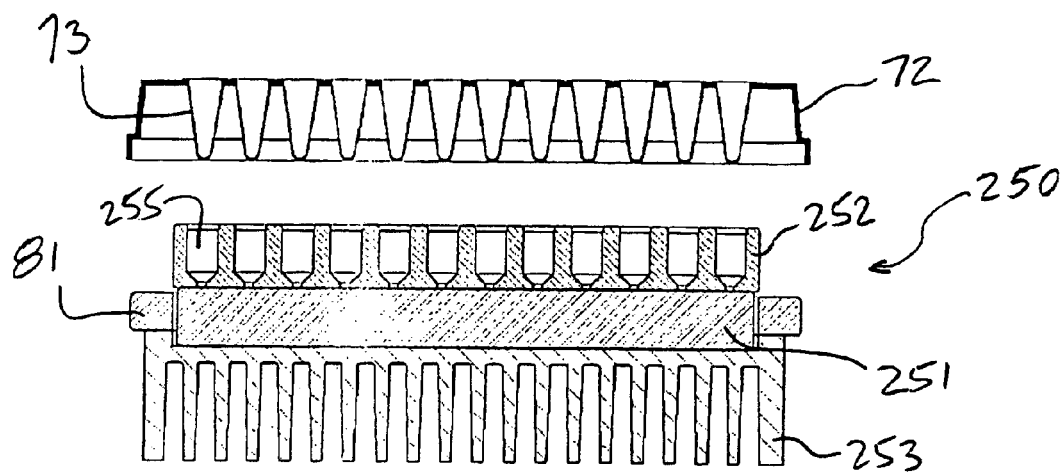
FIG. 5 is a sectional view of the sample preparation device taken along line 5-5 in FIG. 4.

Referring to FIGS. 4 and 5, the PCR sample preparation device includes a heating unit such as a peltier thermoelectric unit 251, which supports on it top an thermal interface structure 252 having complementary wells 255 that are sized to receive the bottom of the wells 73. The peltier thermoelectric unit 251 can be controlled by the controller 68 to heat or cool the wells 73, to subject the contents in the wells 73 to thermal cycling as required by PCR process. At the bottom of the peltier thermoelectric unit 251, a heat sink 253 is provided to remove heat from the peltier thermoelectric unit 251 during the cooling cycle of the unit and/or to remove excess heat during the heating cycle. The PCR sample preparation device 250 is supported on the transport frame 81 of the transport mechanism 80.

Control of the Automated System 200

The system 200 provides easy handling of multi-channel separation columns, and allows easy optical coupling of the detection zones to the detection optics of the CE system 200. The operations of the CE system 200, including the interface mechanism 300, are controlled by a controller 32 interfacing with an external user control interface (e.g., a PC 918). The PCR thermoelectric controller 68 may also be operatively couple to the controller 32 and/or the PC 918, so that the controls of the PCR sample preparation device and the rest of the system 200 are coordinated to achieve the functions described herein are achieved.

Figure 3:
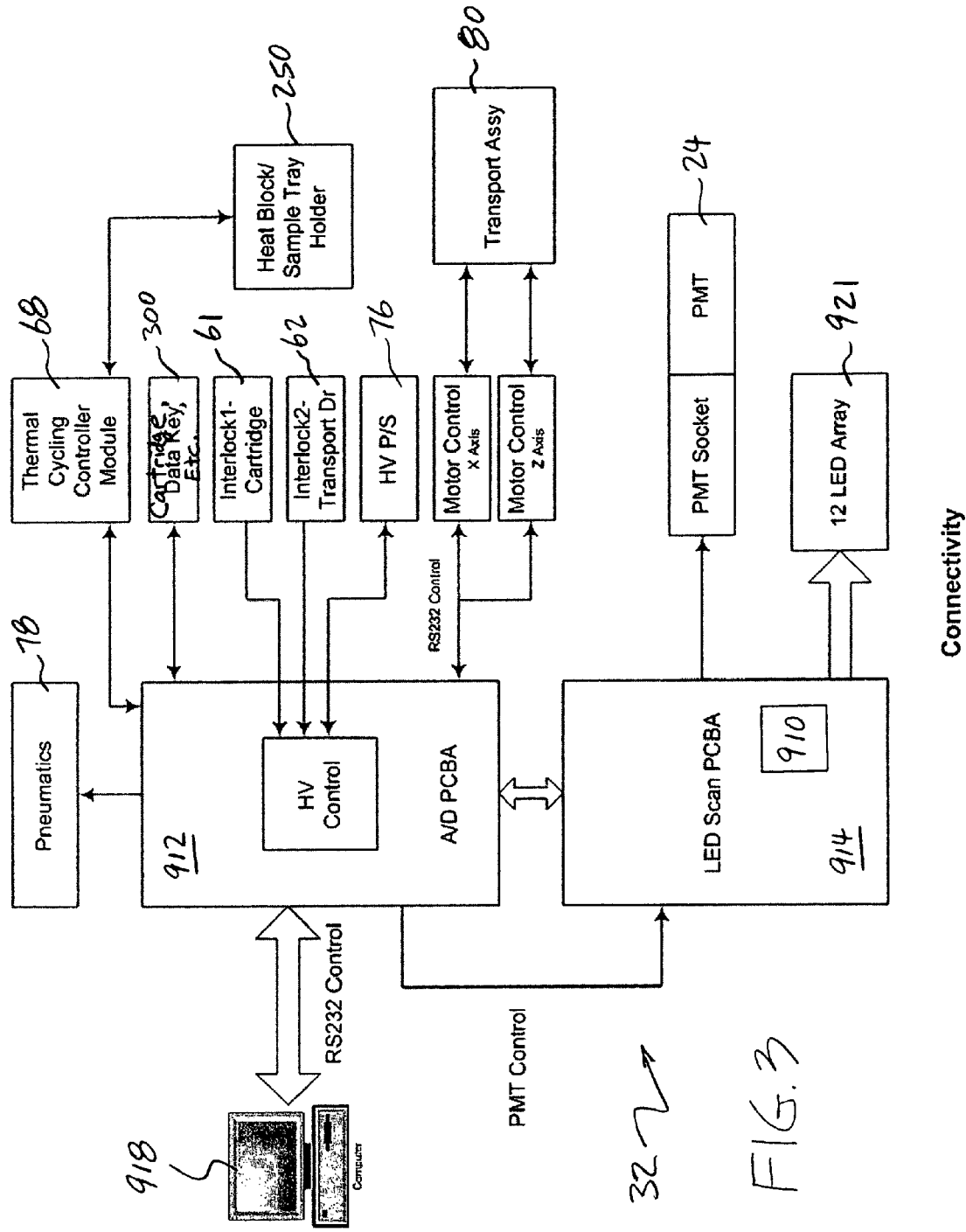
FIG. 3 is a block diagram of the control system for the capillary electrophoresis system in accordance with one embodiment of the present invention.

Referring also to FIG. 3, in accordance with one embodiment of the present invention, the block diagram of the controller 32 for the CE system 200 is illustrated. The controller 32 comprises a processor as part of the A/D Board (LED Processor PCBA) 912 with CPU 910 for converting detection signals received from the detector 24 (e.g., a PMT) to corresponding digital signals, coming from LEDScan PCBA interface 914 for transferring and receiving signals to and from respective parts of the CE system 200 by instructions from the CPU 910. The A/D (LED Processor PCBA) interface 912 is coupled to the various actuators in the interface mechanism 300 to control and connect (using the interface mechanism 300) at least high voltage power supply 76, pneumatics 78 (hidden from view in the interface mechanism 300 in FIG. 2), motor controls (X-Z sample/buffer tray) 80 and interlocks (cartridge and transport doors) 61 and 62 (details of these are not shown in the interface mechanism 300 in FIG. 2). The A/D or LED Processor PCBA 912 also controls the high-voltage power supply 76 for sample injection and electrophoresis functions of the CE system 200, a circuit 914 (LEDScan Board) for modulating the excitation radiation source (e.g., LEDs) 921 and the detector module 24 of the CE system 200. Details of the modulation of the excitation radiation source may be referenced to copending U.S. patent application Ser. No. 10/060,052, which had been fully incorporated by reference herein.

The A/D (LED Processor PCBA) 912 may be further coupled to an external personal computer 918, which in turn performs data processing or additional control function for the CE system 200, e.g., using BioCal's BioCalculator Software to control various features and functions of the automated multi-channel CE system 200 (including the integrated PCR sample preparation device).

The PCR sample preparation device 250 is controlled by the controller 68 to perform the sequence of thermal cycle reaction discussed above. The thermoelectric unit 251, which is supported by the X-Z transport mechanism 80 is designed for 96-well micro titer plate 72. The thermoelectric unit 251 is controlled by the thermal cycling controller module 68, which directly is controlled by the A/D or microprocessor board 912 and the control firmware is controlled by the user interface (BioCalculator software) at the PC 918 via an RS232 cable as shown in FIG. 3. The thermoelectric controller 68 may be incorporated in controller 32, in an alternate embodiment.

The components of the controller 32, with the exception of the PC 918, may be packaged as an electronic board 64 (FIG. 2) and cooling fans 63, on board the CE system 200 and electrically coupled to the PC 918 via a serial port (not shown), or they may be part of a separate controller module outside of the CE system 200. The CPU 210 and/or the PC 218 are programmed to accomplish the various control functions and features for the CE system 200. In one embodiment, the PC 218 can be configured to provide the user control interface for the CE system 200 (e.g., user initiation of the connection sequence of the interface mechanism 300). It would be within a person skilled in the art to implement the program code given the functions and features disclosed herein. In an alternate embodiment, the controller 32 or components thereof may be incorporated as part of the PC 918.

Capillary Cartridge

The multi-channel capillary cartridge 200 includes twelve detection zones (schematically represented as 30 in FIG. 1), defined by capillaries 140 held in a cartridge body. The cartridge 100 includes a twelve-channel fused silica capillary array that is used for separation and detection of the samples as part of a disposable and/or portable, interchangeable cartridge assembly 100. The cartridge 100 shown in FIG. 2 holds up to 12 capillaries 140, 12-18 cm long. The cartridge 100 is integrated with a top, outlet buffer reservoir 130 common to all capillaries 140, which is directly coupled by the interface mechanism 300 to a modular compressed gas source 78, such as a replaceable pressurized gas cartridge of an inert, compatible or non-reactive gas (e.g., Nitrogen, $CO_2$, etc.) or a pressure pump. Appropriate pressure plumbing, including tubing, pressure valve and solenoid controls, is provided. (Details of such plumbing are omitted, since it is well within one skilled in the art to configure such plumbing given the disclosure herein of the functions, features and operations of the system 200.) The pressure source 78 provides the required gas pressure to fill-up all the 12-capillaries with the sieving gel contained in the reservoir 130 and to purge the gel from the previous run from the capillaries during the refilling process. Depending on the viscosity of the gel, pressures of up to 40 PSI may be applied to the capillaries 140 through the gel-filled reservoir 130. The cartridge gel-reservoir 130 is equipped with a built in common electrode anode (not shown) for all 12-capillaries, which is automatically connected by the interface mechanism 300 to the high voltage power supply 76 (FIG. 2) for electrophoresis when installed inside the system 200. A fan or Peltier cooler (not shown) on the adjacent structure to the cartridge 100 may be provided to provide temperature control of the cartridge. In addition or in the alternate, the cartridge may have vent holes (input and output) for air circulation (temperature controlled air to be introduced to the cartridge from the instrument side). Depending on the heat generated during CE separation, the cartridge may simply be exposed to ambient temperature, with no auxiliary cooling features. A power supply 66 (FIG. 2) provides DC power to the CE system 200.

Further details of the cartridge may be referenced to the copending application Ser. No. 10/059,993, which had been fully incorporated by reference herein.

Detection System

U.S. patent application Ser. No. 10/060,052, which had been fully incorporated by reference herein, is more specifically directed to the time staggered/multiplexed detection scheme that can be adopted in the CE system 200.

Interface Mechanism

The structure and operation of the interface mechanism of the CE system 200 may be referenced to the copending U.S. patent application Ser. No. 10/823,382, which had been fully incorporated by reference herein. The cartridge interface accomplishes quick and reliable interface connections to the disposable gel contained capillary cartridge 100. These interface connections include a gas pressurization connection, high voltage connections, and precision optical connections. The interface also provides precise and repeatable mechanical positioning of the cartridge, to accurately position the components of the cartridge in relation to the support elements in the CE system 200, including positioning the capillary tips in relation to external sample or buffer reservoirs, found on 96-well titer plate, for example. Additionally, the interface provides separate electrical, optical and pneumatic connections to each separation channel, thus providing channel-to-channel isolation from cross talk both electrically and optically and insulation to the rest of the instrument from high voltage.

Operation of CE System

In operation, the sample handling tray transport mechanism 80, with a 96-well plate (8×12) 72 and 70, is used to introduce the amplified DNA samples (or analytes) to each capillary 140. The X-Z transport mechanism 80 indexes a row of sample carrying wells 73 in the micro titer plate 72 under the row of capillary tips 140 and dip the tips into the well. By applying a voltage, electrokinetic injection moves a known amount of the DNA sample to the beginning of the separation column 140. After injection, the DNA samples from sample tray 72 may be replaced with a running buffer from tray 70. Alternatively, after injection, the transport mechanism 80 may index to move a row of 12 wells 73 in the titer plate 72 containing buffer solution into position under the cartridge to replace the twelve wells containing DNA samples.

By applying high voltage across the total length of the capillary 140, separation of the DNA sample into DNA fragments is achieved. As the fragments approach the end of the capillaries 140 and enter into the detection zone, the excitation light energy (e.g., from twelve LEDs delivered by optical fibers) is directed at the detection zone, illuminating the migrating DNA fragments. The detection scheme may be in a time-staggered manner as disclosed in copending U.S. application Ser. No. 10/060,052.

To prepare for the next run with a different sample, the old gel from the previous run is purged from the capillaries by pressuring the reservoir to refill the capillaries with fresh gel. The trays 70 and/or 72 carry cleaning solutions, waste collection, and samples. The purged gel is collected by one of the trays 70 and 72 by positioning the tips of the capillaries at a row of waste collecting wells in one of the trays. The tips of the capillaries may be cleaned with water or a cleaning solution by positioning and dipping the tips of the capillaries in such solution in the appropriate tray wells. When the capillaries are refilled and ready for the next run, the tips of the capillary are dipped into the samples by repositioning the tray 72. The above mentioned sequence of process may be programmed as one of the automated functions of the controller 32. The interface mechanism 300 provides the interfacing of support elements in the CE system 200 to the cartridge, such as high voltage, gas pressure, LED radiation source, and detection optics, as described above. Compared to the conventional methods, which utilizes separate PCR machines and electrophoresis (Slab gel or Capillary Electrophoresis) instruments, the new portable automated system is designed to incorporate the combined functions of sample preparation and analysis (e.g., PCR and electrophoresis) as one instrument. The inventive portable micro-fluidic electrophoresis based instrument that comprises an integrated PCR device with a multi-channel and multi-color fluorescence detection system is a reliable tool for a faster and lower in cost genetic analysis type applications.

The inventive system as shown in the FIG. 2 could be a bench top system designed for high throughput biological agent (DNA) detection/analysis. The 12-channel separation/detection cartridge can analyze multiple samples simultaneously. The 12-channel separation/detection cartridge combined with the integrated PCR plate can complete a 96-well sample plate amplification and electrophoresis in much reduced time with predictable results. The system is simple, reliable and fast. The entire process from PCR to DNA separation can be completed in hrs. The analysis time for 12 PCR samples is targeted to be within several minutes. The cost of the proposed instrument would be a factor of 10 lower than the current multiple-channel high-end capillary electrophoresis instruments. In average, the chemistry cost per analysis is estimated to be less than significantly less that the costs for prior art CE systems.

The inventive automated instrument includes the sample handling tray mechanism with an integrated PCR device for the direct nucleic acid molecule amplification, electrophoresis/separation, fluorescence detection, with improved detection for any conjugated dye for immunoassays. The fully automated and portable system is controlled by a general computer. Data analysis for the detected results is automated to give on-the-spot amplification (PCR), peak identification and semi-quantitative analysis. With this new, inexpensive and high-throughput analyzer, the DNA laboratories will have the capability to perform high throughput and rapid bioagent identification with lower in cost, less labor intensive and high accuracy all in one unit. The detection capability of the system can be designed for dedicated detection of certain potential biological agents and pathogens.

In one embodiment of the present invention, the raw samples are introduced to the 96-well titer plate in the thermal cycler, to be subjected to different temperatures (hot and cold thermal cycling process) before, during or after the injection of the samples to the gel-cartridge. The thermal cycler has several purposes or functions during the sample preparation prior to separations and analysis of bio-molecules. One function is for straight PCR amplification of bio-molecules and the other function would be for different temperature cycling of the samples/bio-molecules (sample preparation step) to change the state/condition of the sample prior to electrophoresis with the gel-capillary cartridge. The 12-Channel cartridge could also function as a micro-dispenser. For example one could apply electrokinetic at the first position of the sample tray (position A on 96-well plate) to inject the negatively charged DNA into the capillaries or micro-channels of the cartridge and then the system can reverse the HV Supply polarity to be able to go to position B of 96-well plate to mix the DNA samples (or bio-molecules) from well A with well B (bio-molecule reactions). The cartridge can function as a sample dispenser (liquid dispenser). The heat block could be used to heat or cool any bio-molecules and then electrophoresed and analyzed by the CE cartridge. The bio-molecules (i.e. DNA, RNA, Proteins, Antibody and Antigen) could all be analyzed with the present intergrated sample preparation and electrophoresis mechanism in a very flexible manner. For example one could heat the samples up to 90 degree C. and then drop it to 80 or 70 degree C. and quickly analyze it with the CE cartridge/device in between, before or after the temperature cycling to verify the binding effects of probes with DNA. Or similar to microarray concepts of hybridization, one can manipulate the sample temperatures to wash away the point mutations and then do a quick electrophoresis to quantify it or do a simple quality check of the sample. This approach/process will allow one to check the position of the detected peaks quickly for qualitative work, which is useful in point mutation type detection. The detection sensitivity can be increased by improving the optical detection system of the current fluorescence detection mechanism (i.e. from LED excitation to Laser excitation) to be able to achieve higher detection sensitivity during electrophoresis by reducing to a less number of thermal cycling (PCR) steps with the heat block. With this thermoelectric module one could also store the PCR-ed samples at a lower set temperature for storage or preservation purposes. With the inventive process, the PCR steps could be simplified to detect the right or wrong detected fragments (mutation analysis) or single strand analysis or analysis of proteins due to temperature change. This system of thermal cycling block/process for sample preparation could also be used as a PCR step/process of injected samples inside the capillary tubes. One could simply inject the samples electrokineticaly from one sample well, then go to another well, which has oil in it and dip the capillary tips inside the oil and start the temperature cycling of the injected samples inside the micro-channels (inside capillary PCR) and then do electrophoresis. This system of multi-channel capillary electrophoresis combined with thermal cycling features (sample plate heat block) of the sample plate for sample preparation will provide flexibility similar to microarrays or real-time-PCR type devices for complete and an one stop solution of bio-molecules analysis.

While the invention has been particularly shown and described with reference to the preferred embodiments, it will be understood by those skilled in the art that various changes in form and detail may be made without departing from the spirit, scope, and teaching of the invention.

The sample preparation station may be configured to undertake processes other than PCR to produce samples in a form suitable for CE analysis. The automated system 200 may be configured to conduct other types of analysis different or in addition to CE separation and analysis. For example, for protein or bioagent detection, immunoassays combined with the micro-fluidic electrophoresis system could also be used. Protein extract from cultures is used for immunoassays. The amplification signals via interaction of antigen and antibody conjugated fluorescence dye is automatically applied to a multi-channel cartridge for high-resolution detection within several minutes.

Interface mechanisms may be adapted to receive capillary cartridges of other structural designs. A person skilled in the art will recognize that the instrument incorporating the essence of this invention can also be used for bio-molecular analysis other than DNA analysis. For example, by altering the separation gel or buffer, the instrument can also be modified to analyze biomolecules like proteins, carbohydrates, and lipids.

By way of example and not limitation, the detection scheme of the present invention is described in connection with capillary electrophoresis and radiation induced fluorescence detection. It is understood that the present invention is also applicable to detection of analytes separated based on bio-separation phenomenon other than electrophoresis, and detection of radiation emissions other than fluorescence emissions, including other types of emissive radiation, such as phosphorescence, luminescence and chemiluminescence, as well as absorbance based detection.

Furthermore, while the separation channels in the described embodiments are defined by cylindrical columns or tubes, it is understood that the concepts of the present invention is equally applicable to separation channels defined by channels, for example micro-channels (such as square, rectangular or essentially semicircular cross sections) defined by etching in a substrate (micro-fluidics type devices or bio-chips).

The transport mechanism can be configured to move the trays in a horizontal plane, and an additional transport mechanism may be provided to move the trays vertically to access the trays.

The sample output from the sample preparation device may be input to an analysis devices without necessarily being subject to separation.

Accordingly, the disclosed invention is to be considered merely as illustrative and limited

We claim:
1. A bioanalysis system, comprising:
a sample preparation device, receiving a raw sample to be processed into a sample in a form suitable for subsequent analysis; and
a sample analysis device, receiving the sample from the sample preparation device to be subject to analysis;
wherein the sample preparation device and the sample analysis device are operatively coupled within an integrated automated system, whereby sample output from the sample preparation device is input to the sample analysis device without further user intervention.
2. The bioanalysis system as in claim 1, wherein the sample analysis device comprises separation capability that separates the sample into components.

3. The bioanalysis system as in claim 2, wherein the sample analysis device further comprises detection capability providing analysis of the separated components.

4. The bioanalysis system as in claim 3, wherein the sample analysis device comprises capillary electrophoresis that provides separation and detection capabilities.

5. The bioanalysis system as in claim 1, wherein the sample preparation device is structured and configured to subject the raw sample to a bio-molecular reaction.

6. The bioanalysis system as in claim 5, wherein the sample preparation device is structured and configured to provide thermal cycling processing of the raw sample to output a sample that is amplified from the raw sample.

7. The bioanalysis system as in claim 1, wherein the sample preparation device comprises a thermoelectric unit that is controlled to cycle the temperature of the raw sample to cause a bio-molecular reaction.

8. The bioanalysis system as in claim 7, wherein the sample preparation device is structured and configured to effect DNA amplification by PCR in the bio-molecular reaction.

9. The bioanalysis system as in claim 8, wherein the analysis device comprises a capillary electrophoresis system.

10. The bioanalysis system as in claim 9, wherein the capillary electrophoresis system comprises multi-channel separation and analysis.

11. The bioanalysis system as in claim 10, wherein the raw sample comprises DNA extracted from a field sample.

12. The bioanalysis system as in claim 9, wherein the raw sample is loaded into a sample well in the sample preparation device, and further comprising an integrated transport mechanism to position the sample well to be accessible by the capillary electrophoresis system.

13. The bioanalysis system as in claim 1, wherein the raw sample is loaded into the sample preparation device, and further comprising an integrated transport mechanism to position the sample preparation device to be accessible by the sample analysis device.

14. The bioanalysis system as in claim 1, wherein the sample preparation device comprises a device for effecting thermal cycling.

15. A PCR system, comprising:
- a thermal cycler performing PCR, receiving a raw DNA sample to be amplified into a DNA sample by PCR, in a form suitable for subsequent analysis; and
- a capillary electrophoresis system, receiving the DNA sample from the thermal cycler to be subject to capillary electrophoresis to analyze result of the PCR;
- wherein the capillary electrophoresis system and the thermal cycler are operatively coupled within an automated integrated system, whereby DNA sample output from the thermal cycler is input to the capillary electrophoresis system without further user intervention.

16. A process for analyzing a raw sample, comprising the steps of:
- providing a sample preparation device, which receives a raw sample to be processed into a sample in a form suitable for subsequent analysis; and
- providing a sample analysis device, which receives the sample from the sample preparation device to be subject to analysis;
- wherein the sample preparation device and the sample analysis device are operatively coupled within an integrated automated system, whereby sample output from the sample analysis device is input to the sample preparation device without further user intervention.

* * * * *